United States Patent [19]
Reis et al.

[11] Patent Number: 4,887,019
[45] Date of Patent: Dec. 12, 1989

[54] DEVICE FOR THE GENERATION OF A LASER BEAM SPOT OF ADJUSTABLE SIZE

[75] Inventors: Werner Reis, Munich; Werner Bisle, Neuried, both of Fed. Rep. of Germany

[73] Assignee: G. Rodenstock Instruments GmbH, Munich, Fed. Rep. of Germany

[21] Appl. No.: 49,979

[22] PCT Filed: Sep. 11, 1986

[86] PCT No.: PCT/DE86/00360
§ 371 Date: Jul. 13, 1987
§ 102(e) Date: Jul. 13, 1987

[87] PCT Pub. No.: WO87/01819
PCT Pub. Date: Mar. 26, 1987

[30] Foreign Application Priority Data

Sep. 11, 1985 [DE] Fed. Rep. of Germany ....... 3532464
Mar. 12, 1986 [DE] Fed. Rep. of Germany ....... 3608242

[51] Int. Cl.$^4$ ............................ G02B 26/10; A61B 3/10
[52] U.S. Cl. ..................................... 350/6.1; 350/6.4; 350/6.9; 351/209; 351/221; 128/303.1
[58] Field of Search ............... 350/6.1, 6.5, 6.6, 6.7, 350/6.9, 6.91, 174, 6.2, 6.3, 6.4, 6.8; 351/209, 211, 221, 243; 250/235, 236; 128/303.1

[56] References Cited

U.S. PATENT DOCUMENTS

| | | |
|---|---|---|
| 3,460,880 | 8/1969 | Henderson ........................ 350/6.5 |
| 3,479,107 | 11/1969 | Blythe et al. ....................... 350/6.6 |
| 3,703,176 | 11/1972 | Vassiliadis et al. ................ 351/221 |
| 4,081,207 | 3/1978 | Dippel ................................ 350/6.4 |
| 4,175,832 | 11/1979 | Umeki et al. . | 
| 4,241,257 | 12/1980 | Koester ............................. 350/6.7 |
| 4,283,116 | 8/1981 | Weis .................................. 350/174 |
| 4,443,075 | 4/1984 | Crane ................................ 351/209 |
| 4,538,608 | 9/1985 | L'Esperance, Jr. ............. 128/303.1 |
| 4,626,063 | 12/1986 | Honey ................................ 350/6.9 |
| 4,732,148 | 3/1988 | L'Esperance, Jr. ............... 351/221 |
| 4,743,107 | 5/1988 | Aizu et al. ......................... 351/221 |

FOREIGN PATENT DOCUMENTS 0143743 6/1985 European Pat. Off. .
0151869 8/1985 .
2111716 7/1983 United Kingdom .

Primary Examiner—Bruce Y. Arnold
Assistant Examiner—Loha Ben
Attorney, Agent, or Firm—Antonelli, Terry & Wands

[57] ABSTRACT

A device for the generation of a laser beam spot of adjustable size on an object, in particular in the human eye so as to enable laser surgery of the eye. The device includes a focusing device which projects the laser beam onto the eye with a small focusing spot and a large aperture cone and a deflector device which moves the focusing spot over the desired beam spot area in a predetermined scanning pattern. In this way, it is possible, for example, also to realize large treatment areas of any desired shape on the fundus without any injury to the frontal eye sections.

32 Claims, 6 Drawing Sheets

DEVICE FOR THE GENERATION OF A LASER BEAM SPOT OF ADJUSTABLE SIZE

DESCRIPTION

1. Technical Background

The invention relates to a device for the generation of a laser beam spot with adjustable size.

In working processes or in therapeutic processes with lasers, for example in cutting processes or in operations in the human eye, there exists the general problem of adjusting the laser beam, which will have a certain cross-section depending on the type of laser used, to the surface to be worked or to be treated.

2. State of the Art

To do this, particularly in the medical technique sector, beam-expanding optical elements are used in conjunction with elements, for example, vario-lenses, which alter the magnification. In this way, it is, for example, possible to vary the beam spot area of the operation laser on the fundus between certain diameters. However, this raises the problem that at the same time the aperture cone of the beam is also varied. If this aperture cone becomes too small, then the energy density is already so great before the actual operation site that it may cause injury. In addition, it is not possible with these known devices to set more or less any desired beam spot areas such as, for example, are required for incisions in the cornea which can, for example, be performed by EXIMER lasers.

REPRESENTATION OF THE INVENTION

The object of the invention is to describe a device for the generation of a laser beam spot with which, for example, injuries to the cornea or the iris due to high radiation intensity can be safely avoided even with spot sizes of greatly differing size and with which, in addition, any desired spot forms can be generated.

In accordance with the invention, burns etc. on areas in front of the area to be treated are avoided by working with a laser beam with an aperture cone of constant size while the area to be irradiated on the object is not irradiated with a stationary laser beam of relatively high energy but is swept over by the laser beam in accordance with a predetermined pattern. According to the setting of this sweep-over movement spot sizes of different sizes can thus be realized. The size of these beam spots can be varied infinitely in accordance with the selected scanning pattern which ensures a zoom-like adjustability. In this way an adjustable zoom optical system can be dispensed with and it is even perhaps possible to have a smaller adapter construction. But injuries are still effectively prevented as the aperture angle of the irradiation cone always remains constant and thus the energy density in front of the coagulation area does not vary.

For coagulations on the fundus, a laser beam spot size of 50 $\mu$m, with which a larger laser beam spot is scanned, has proved to be particularly useful. Depending on the type of optical system used, on the laser source and also on the application sector, other spot sizes are, of course, also possible and sensible.

Particularly in eye operations, a circular beam spot is preferred. Here the relationship of the irradiated area to the area to be treated is particularly favourable; this spot configuration is, in addition, particularly advantageous for heat dissipation. However, depending on each application case, other spot forms, for example square forms, can also be selected.

The scanning of the spot can, for example, be in a linear form. In accordance with the invention it is, however, also preferred to process a circular beam spot with a rotating laser beam, i.e. the laser beam rotates on a ring-shaped path. By increasing the path diameter, the desired spot size is obtained. The adjustment of the spot size can be done automatically or manually in full accordance with the requirements. The rotation movement of the laser beam is advantageously done automatically with a normal rotation time being around 8 msec. However, this value should not be understood as a limitation.

To obtain a certain distribution of the power over the beam spot area, for example a Gaussian distribution or a homogeneous or uniform illumination of the beam spot, a number of different measures can be taken. In particular, it is possible to vary the power of the laser beam according to local variations.

For example, to obtain a uniform illumination, it is possible to increase the power of the laser beam with increasing circular ring diameter. In this case, no mechanical measures need to be taken. Depending on the specific requirements, this means that the energy of the laser irradiation can be continuously increased or decreased towards the rim of the beam spot.

In accordance a feature of the invention, there is a further possibility of having the laser beam rotate more slowly so that the longer rotation path of the laser beam at the rim of the beam spot will be compensated for by a correspondingly higher exposure time.

The scanning movement in accordance with the invention can, of course, be performed in the most varied fashion, for example by acousto-optical deflector elements. However, the device in accordance with the invention preferably has an element with at least one moveable optical part with this element advantageously being designed as a tumbling unit, i.e. one which can simultaneously perform a movement through two axes. The optical part(s) in question are preferably plano plates or mirrors.

In one version example of the device in accordance with the invention, two swivel plano plates positioned one over the other are used for the optical parts (claim 10) where the swivel axes of the plates form an angle with each other and which are preferably swivelled to and fro out of phase by a drive unit. For this purpose it is useful if the axes of the two plano plates are positioned with respect to each other at an angle of 90° and if the two plano plates are driven by means of an angle engine with signals, preferably sinusoidal signals which are in phase quadrature with each other. With this synchronized deflection by means of the two plano plates, the laser beam can be transposed into a circular rotation movement.

In another advantageous version example of the invention, the optical part has at least one mirror. With two mirrors whose swivel axes form an angle of 90°, an x/y scanning of the desired beam spot can, for example, be obtained. Furthermore, it is possible to use a mirror which is rotated through one swivel axis and tilted through a different swivel axis. By means of the rotation movement of the mirror, a rotation of the laser beam is generated in turn with the diameter of the circular ring swept over by the laser beam being able to be infinitely varied by tilting the mirror. By means of a revolution control of the engine which rotates the mirrors, the irradiation power incident to the beam spot can be adjusted infinitely.

In a further version example of the invention a rotating, tiltable glass plate is used as the optical element which deflects the laser beam and shifts it into a circular movement with a diameter which can also be adjusted. Due to the continuous increase of the tilt, a spiral-shaped movement of the laser beam can, of course also be generated. Alternatively, a line by line grid scan is also possible.

To obtain the most exact control of the laser beam possible and to have the largest possible moveability of the optical part, the optical part is preferably mounted in gimbals so that tilt movements in any direction are possible. In this way, a mounting largely free of play and friction becomes possible with which radial twists are prevented. In accordance with the invention, the tumbling unit can be a mechanical device.

Preferred is a realization of the tumbling movement by electromagnetic means. This permits the array to be designed with few wear parts and makes possible a fast adjustment of the desired position of the optical part. The part of the device mounted in gimbals consists of permanent magnets which have permanent magnets with opposing poles positioned opposite them and which stabilize the tumbling body in the rest position. On the other side, magnetic coils are preferably positioned which are activated out of phase to each other and which exert attracting moments on the tumbling body both locally and temporally displaced. In this way, an exact circular tumbling motion of the optical part can be produced.

Of use for this purpose is a shifting of the universal joint of the array towards the center so that the masses moved during tumbling can be kept small which will result in a higher mechanical resonance frequency of the array. A further improvement in this regard is a reduction of the masses moved. In this way, it can be achieved that the tumbling frequency is at a safe distance below the resonance frequency of the mechanical array. Due to the spot size and to the effect of the laser spot on the retina, a maximally required tumbling frequency of around 20 Hz is produced.

Mechanical stops can be provided to advantage to prevent the magnets from sticking on large excursions of the tumbling array, i.e. from sticking to the opposite permanent magnets or poles of the electromagnets. Another measure to solve this problem can consist of arranging the fixed position magnets in such a way that they are aligned face to face at maximum excursions. In a preferred version example, the device in accordance with the invention can be operated in three different ways: in manual operation where the tumbling movement can be reproduced step by step; semi-automatically with the tumbling movement being able to be stopped or, alternatively, the tumbling radius being able to be readjusted; and fully automatic. In the last operation method, any desired pattern can be projected, if a fast shutter is used even punctual patterns, for example a row of points arranged in accordance with a certain pattern where the size of the points corresponds to the diameter of the laser beam or is even larger.

When working lasers are used whose light is not in the visible part of the spectrum, i.e. either in the UV or the infra-red sectors, it has been usual for quite a long time to use a so-called target light source. With medical operation lasers the beam of the target light source in this process is positioned flush with the beam of the operation laser so that the doctor can check whether the beam of the operation laser is set to the area to be treated before the operation.

However, this also causes the problem that the beam of the target light source outshines sensors, for example image sensors with which the fundus is analyzed, so that not details of the fundus can be resolved.

In accordance with the invention it has now been recognized that the general invention idea behind this application of scanning a pre-determinable area with a beam focused on a small sector also permits a solution to this problem.

In contrast to the known solutions, in which the target light beam and the working light beam are guided flush to each other, the target light beam is in accordance with the invention moved on a path which surrounds the beam spot of the working light beam. In this way, it is still possible to check whether the working light beam, i.e., for example, the beam of an operation laser, is set to the correct spot; as, however, the target light beam surrounds the area to be worked or to be treated, structures of this area are not outshone by the light of the target light beam, for example of a helium neon laser.

The path on which the target light beam is guided can be adapted to any spot dimension of the working light beam in this process. If the working light beam, for example the beam of an EXIMER laser, is used e.g. for incisions in the cornea, then the target light beam can surround the total (lengthways) sector on which the working light beam is guided for scanning. In the case of coagulations, it is, of course, possible to guide the target light beam on a ring-shaped course which surrounds the beam spot of the working laser in a ring form. Additionally, the laser may be a Neodym-YAG laser or a laser with a radiation wavelength of approximately 3 $\mu$m.

The device in accordance with the invention can, of course, be used for any desired laser and any desired objects to be treated, for example in material working, in vascular operations, etc. However, it is particularly advantageous to use the process in accordance with the invention for operations on or in the eye as here the energy density of the beam in front of the operation site is particularly important, as is the possibility of still being able to resolve the smallest structures in the area to be treated.

BRIEF DESCRIPTION OF THE DRAWING

The invention is described further in the following by means of preferred version examples and of the drawing. In the drawing:

FIG. 2a and 2b show two further version examples of the device in accordance with the invention where the optical part is a mirror.

In FIG. 1(a) and 1(b) a first version example of the device in accordance with the invention is shown. In the beam path of the laser, which is marked with the arrow 10, there are two identical rectangular plano plates which are arranged one over the other at a distance to each other. The two plano plates 20, 22 are positioned one above the other in this process in such a way that they overlap each other with a part of their surfaces with their longitudinal axes forming an angle of 90° with each other and where the laser beam passes through the overlapping range substantially in the center of this. In the extension of their longitudinal axes, the two plano plates 20, 22 are each provided with a shaft section 24, 26 each of which is, in turn connected to a drive engine, e.g. an anqle engine 28 or 30. In the version example shown, the two plano plates are both swivelled through 10° from the horizontal axis in both directions. In this process, the axis of the shaft section 24 is termed the X axis and the axis of the shaft section 26 the Y axis. The two axes are controlled with signals staggered at 90° to each other. In the version example shown, these are sinusoidal signals, as is intended to be shown by the addition of "sin" and "cos" for sine or cosine in the drawing. The relationship is demonstrated in the schematic figure in FIG. 1(b) by two sine curves x and y which are drawn in displaced fashion with reference to each other.

Figure 1B:
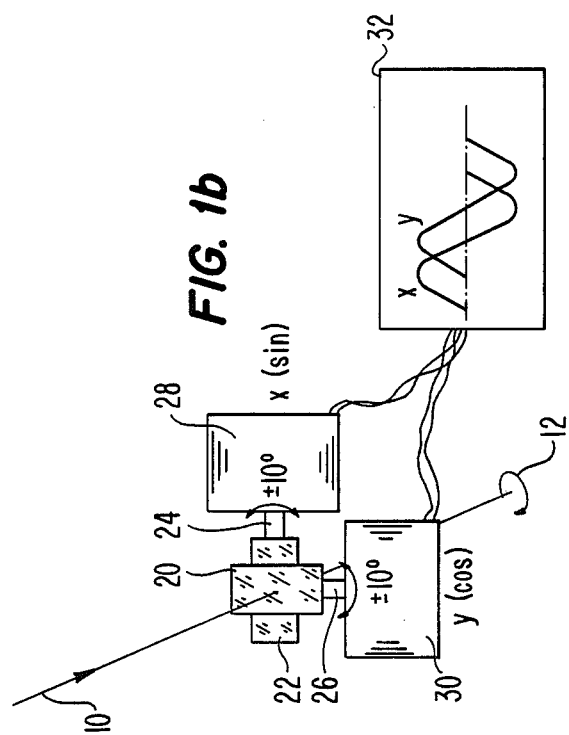
FIGS. 1a and 1b show a first version example of the device in accordance with the invention which has two swivel plano plates positioned one above the other as the optical parts.
Figure 1A:
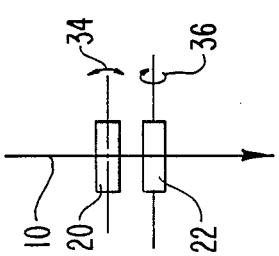

While FIG. 1(b) as a top view of the plano plate arrangements illustrates the relative positions of the swivel axes 26 and 24 to each other, in FIG. 1(a) the different swivel movements of the two plano plates 20 and 22 are further demonstrated with the arrows 34 and 36. Arrow 10 illustrates the beam path of the laser beam for stationary plates. Due to the out-of-phase swivelling of the two plano plates, the laser beam is deflected in such a way that it performs a circular rotation movement. This is illustrated in FIG. 1(b) (bottom) by the circular arrow 12.

Figure 2A:
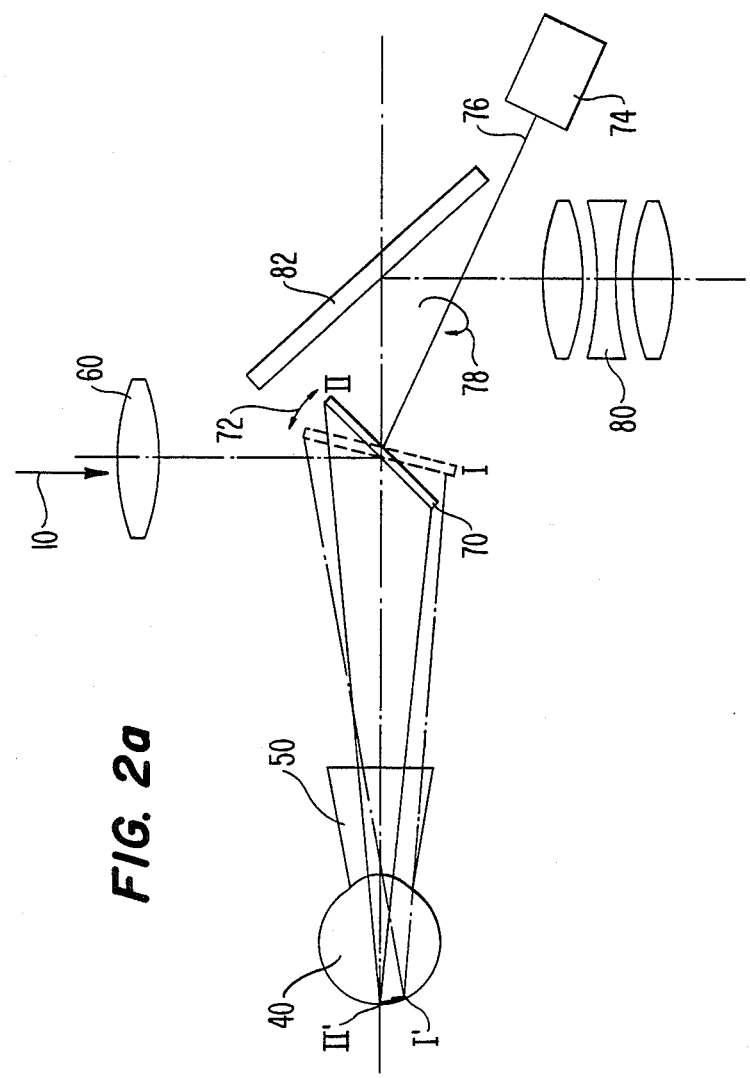

FIGS. 2(a) and 2(b) show two version examples of the device in accordance with the invention where a mirror is used as the optical part. We will first describe FIG. 2(a). An expanding optical system 60 serves to broaden the laser beam. Behind this expanding optical system is a rotating, tiltable mirror 70 which is shown in two tilt positions I and II with arrow 72 illustrating the tilt movement between the positions I and II. The expanding optical system has been designed in such a way that the laser beam on the mirror 70 has a diameter of about 10 mm and forms a beam spot on the fundus of the eye 40 of about 50 μm. The different tilt positions I and II are matched by the different postions of the beam spot in the vertical direction of the fundus; this is illustrated by the markings I' and II'. An engine 74 is connected with the mirror 70 by a rotation axis arrangement 76 and this engine brings the mirror into a very fast rotation movement and tilts it at the same time, as is illustrated by arrows 72 and 78. The number of revolutions of the engine 74 can be controlled and the engine is infinitely tiltable so that the diameter of the area on the fundus swept over by the laser beam can be infinitely varied which permits the spot sizes on the fundus to be realized in any desired size. If, for example, a conventional engine rev count of about 8,000 r.p.m. is selected, then a ring zone can be swept over once in about 8 msec.

In FIG. 2(a) the illumination beam path is also shown in schematic form. A lens 80 serves as gap illumination. The illuminating light is deflected towards the eye by a deflector mirror 82 and enters the eye via the contact glass 50 and illuminates the fundus. This illumination beam path is of a conventional type.

FIG. 2(b) shows another version example with a mirror as the optical part. Where identical parts are used in the arrangement, these are also designated with the same reference marks. The laser beam 10 is again directed through an expanding optical system 60 but is then not guided directly onto the mirror 70 but first directed onto the mirror 70 at an angle of 90° through a fixed-position deflector mirror 62. For the drive of mirror 70, an engine 74 with revolution control is again provided so that the mirror can perform a rotational movement (arrow 78) and a tilt movement (arrow 72). On exiting from this mirror, the rotating laser beam does not directly enter the eye 40 but rather first is directed through a prism 86 to a mirror 88 from which it is reflected towards the eye 40.

The illuminating light (cf arrow 92) is first directed through a lens head 84 and a lens element 80 to a deflector prism 82' where it is reflected and directed through the semi-transmitting mirror 88 and the prism 86 towards the eye 40. After passing though prism 86, the laser light and the illumination light in this version example enter the human eye from substantially the same direction. This is illustrated with arrow 90.

Figure 3:
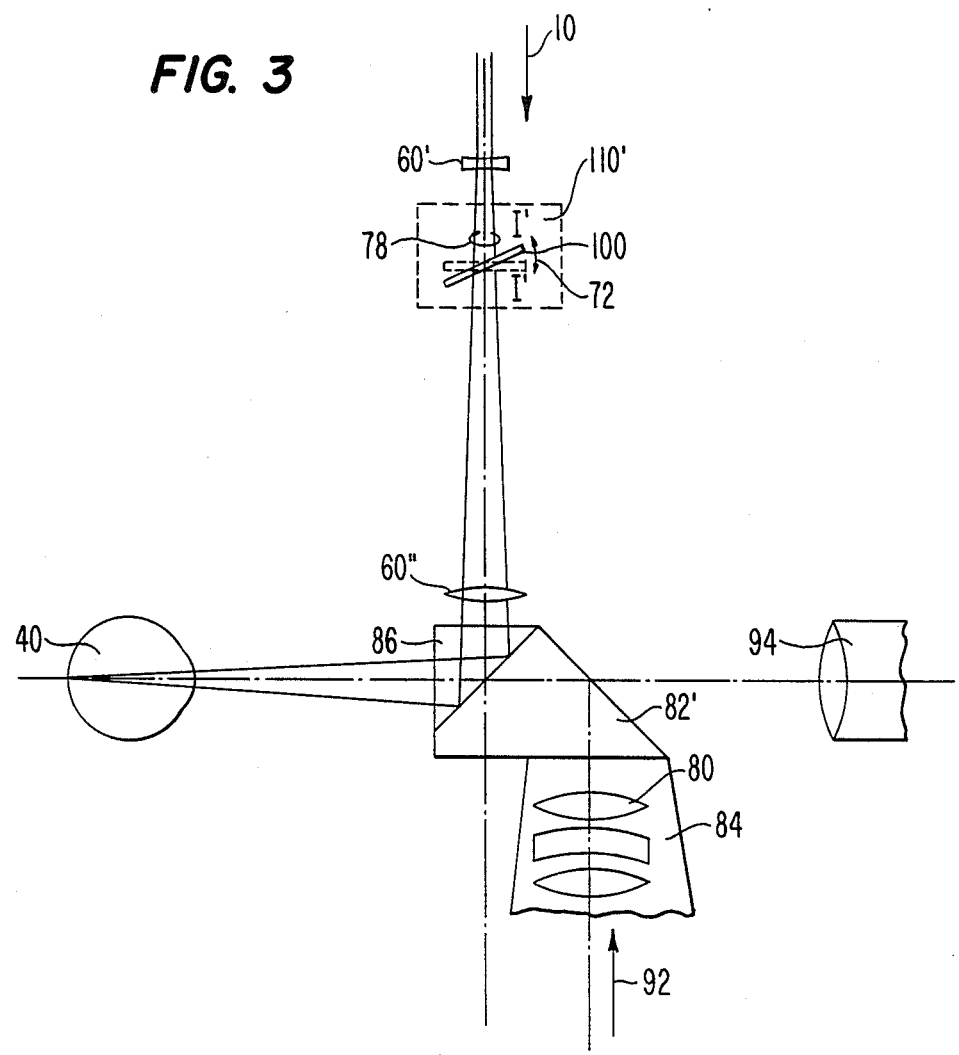
FIG. 3 shows a further version example of the device in accordance with the invention where the optical part is a glass plate.

In FIG. 3 a version example of the device in accordance with the invention is illustrated where the optical part is a plano plate which, like the mirror, can be swivelled or tilted, as is illustrated by the arrows 72 and 78 and the position markings I' and II' respectively. The glass plate is held in an arrangement 110 and mounted, as is explained in detail below. As in the previous version examples, identical parts are marked with identical references. The expanding optical system in this version example comprises two elements 60' and 60''. The beam illumination path is constructed in the same way as in FIG. 2b.

In addition, a microscope 94 is positioned to the right of the prism 82' from where the fundus of the eye 40 can be observed substantially in a straight line through the prism 82' and the prism 86. In this version example, too, the laser beam is deflected from its rectilinear alignment and sent into a circular movement by the tumbling motion of the glass plate 100 with the diameter of the circular movement being adjustable by the selection of the tilt angle of the glass plate 100.

Figure 4:
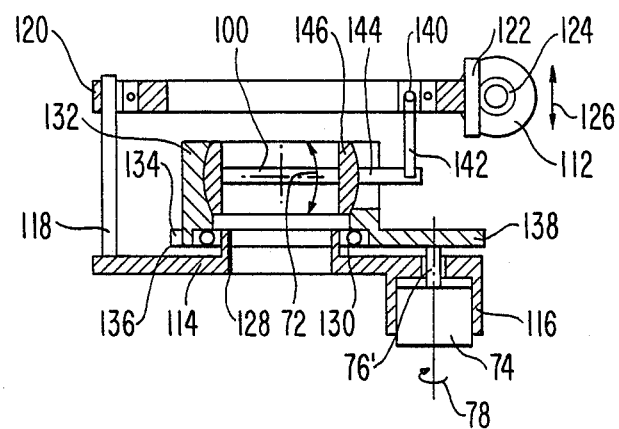
FIG. 4 shows an example of a holder and a mounting for the glass plate shown in FIG. 3.

FIG. 4 shows a version example of a holder and drive arrangement of the glass plate 100 which is shown in FIG. 3.

A housing plate 114, which is essentially in a circular disc form and which is positioned concentrically to the beam path of the laser beam, possesses on an external side in the direction of the beam of the laser flange-like protrusions 116 which point downwards and which hold a first engine 74 which is provided for the rotation movement of the glass plate 100, as is illustrated by arrow 78 and which will be described in detail below. On the side opposite to the engine 74 the housing plate 114 possesses three guide rods 118 set at angles of 120° to each other which are aligned towards the laser beam source, i.e. in opposite alignment to the engine 74. In the area of the extreme end of the guide rods 118 a plate 120 is held which has a central aperture and which is aligned parallel to the housing plate 114. In a rim area the plate 120 possesses a cog rack 122. Meshed with this cog rack 122 is a first cogwheel 124 which forms the part of a gear of a second engine 112. The engine 112 serves to set the height of the plate 120, as is illustrated by arrow 126.

On the side opposite to the first engine 74, the housing plate 114 possesses a flange ring 128 which limits the central aperture and on whose exterior side a ball bearing 130 is positioned which meshes with the flange 128 (which points downwards) of a cylindrical bearing. The cylindrical bearing has such an exterior diameter that it is positioned with reference to the guide rods 118 within and at a distance to these, and it has such a height that it is positioned at a distance with reference to the plate 120. The first engine 74 is connected via a shaft 76' with a second cogwheel 138 which meshes with the teeth 136 on the exterior of the flange 134 of the cylindrical bearing 132. Thus, if the first engine 74 rotates, then the result is that the bearing arrangement 132 also rotates.

Radially within the guide rods 118 the plate 120 is provided with a ball bearing 140 in which reposes an arm 142 of a bar structure comprising two arms connected to each other in an articulated fashion. Here, the arm 142 is aligned downwards in the rest position in FIG. 4, i.e. axially to the laser beam. The second arm extends in the rest position horizontally radially inwards into a bearing 146 which is designed as a swing bearing. The swing bearing 146 is essentially cylindrical in form, has a hollow inside and an arched exterior surface which meshes with a correspondingly formed arched inside surface of the bearing 132. The swing bearing 146 is connected to the cylindrical bearing 132 by means of a second bars structure arm 144. The glass plate 100 is in a fixed position in the swing bearing 146.

The arrangement described above works in the following way: The glass plate 100 is set to rotate by the first engine 74 with the drive being transmitted via the teeth 136 and the cogwheel 138 and said drive being low in friction due to the ball bearing arrangement 130. The swing bearing 146 of the glass plate is connected to rotating cylindrical bearing 132 by the second arm 144 of the bar structure, whereby this arm serves as a carrier. By means of the bar structure 142, 144 the glass plate 100 can be brought to a defined angle position. In this process, the bar structure also makes the rotation with it reposing in the second ball bearing 140. This second ball bearing 140 has its height set by means of the cog rack 122 and a gear arrangement consisting of the cogwheel 124 and the engine 112. In this way, the swing bearing 146, which is positioned movably in the cylindrical bearing 132, is positioned more or less diagonally and accordingly, the glass plate 100 is brought into a more or less highly diagonal position, as is illustrated by arrow 72. In this process, the guide rods 118 serve to set the exact height of the plate 120. By means of this arrangement the glass plate can thus be rotated and tilted in a similar fashion to the mirror in FIGS. 2a and 2b and the glass plate in FIG. 3. In this way, a rotating laser beam is generated on the fundus with a different radial distance from the beam axis of the non-deflected laser beam being generated by a corresponding tilting of the glass plate.

Figure 5:
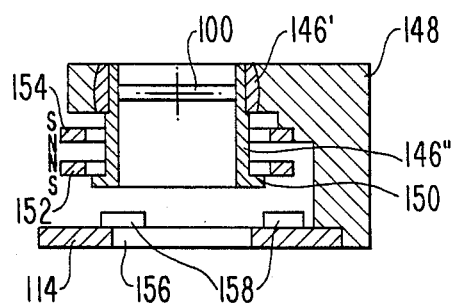
FIG. 5 shows a further example for the holder and mounting of the glass plate shown in FIG. 3, FIG. 6a to 6c show detailed representations of the holder arrangement shown in FIG. 5.

FIG. 5 shows an alternative arrangement to that shown in FIG. 4. In a housing 148, which possesses a coaxial aperture central to the laser beam direction, a swing bearing 146' with spherical exterior walls and cylindrical interior walls is positioned. The swing bearing 146' reposes in the housing 148 and can be rotated or swivelled. In the interior of the swing bearing, a cylindrical hollow body is fixed in position which extends downwards in an axial direction and in which the glass plate 100 is held fast at the height of the swing bearing with low axial extension. The housing 148 is designed in such a way that it holds the swing bearing 146' at a protruding section so that this like the cylinder 146'' is freely movable and cannot come into contact with the housing 148 in any position. The cylindrical holder 146'' is provided with a flange 150 on the end opposite to the swing bearing 146', said flange points outwards and with a ring magnet arrangement 152 reposing on it. In this process, the ring magnet arrangement is designed in such a way that the north pole points upwards and the south pole downwards. At an axial distance above this ring magnet arrangement reposes a second ring magnet arrangement 154 with poles positioned reversely, i.e. the north pole points downwards and the south pole upwards so that the two ring magnets repel each other. In this process, the second ring magnet arrangement is fixed in such a way that it sits fast on the housing 148 and does not mesh with the cylinder 146'' but with the two ring magnets being axially located one above the other. At the bottom of the housing is a cylindrical housing plate 114 which also has a central aperture 156 and possesses coils 158. In the version example shown three coils are arranged at distances of 120' on the housing plate 114 which serves as the coil carrier.

The arrangement shown in FIG. 5 works in the following fashion: A defined current is impressed out of phase over the coils 158. The ring magnet 152, which is connected in a fixed position to the holding cylinder 146'', is thus repelled by the coils. As a result of the 120° coil arrangement, a circular tumbling effect is produced similar to an engine controlled by three-phase current. The second ring magnet 154, which is connected to the housing 148, creates a counter-power to the coil 158 due to its defined repulsion with reference to the first ring magnet 152. In this way, the angle position, i.e. the tilt position of the glass plate 100, can be set exactly. Depending on the strength of the current set in the coils, the angle position of the glass plate can be set via the swing bearing 146'. Again, in this way, a rotating laser beam with adjustable radius can be generated.

Figure 6A:
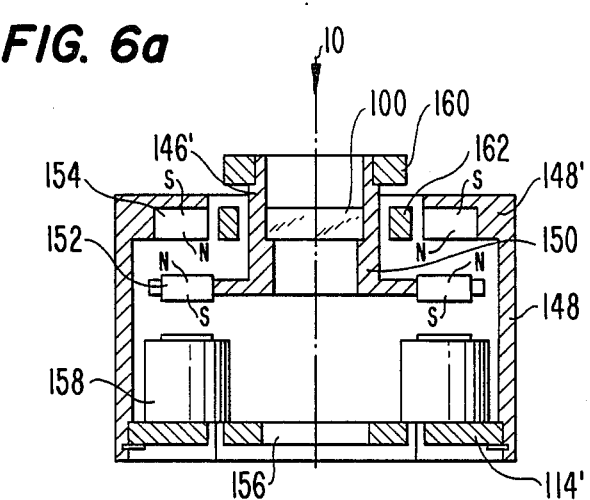
Figure 6B:
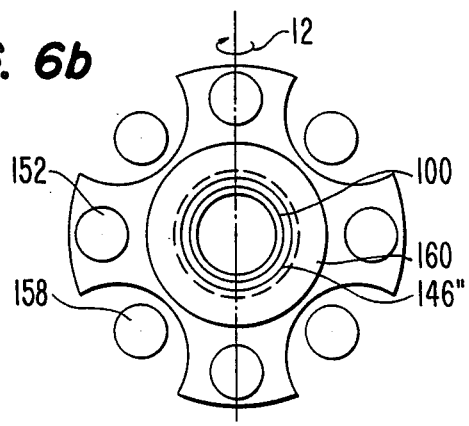
Figure 6C:
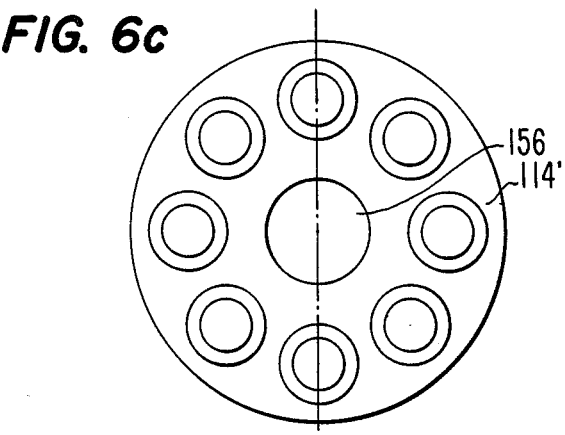

FIGS. 6a to 6c show an alternative arrangement to that shown in FIG. 5 for the realization of a tumbling movement by electro-magnetic means. The cylindrical holder 146'' of the plano plate 100 is mounted in gimbals so that tilt movements in any direction are possible. This is possible by means of an intermediate cage 162 provided at the height of the glass plate 100 and by means of the housing 148 which surrounds the holding cylinder 146'' at a distance to this. The cylindrical holder 146'' has at its lower end in FIG. 6a a radial flange 150 which extends outwards and which carries four permanent magnets whose north poles face upwards. The housing 148 possesses at the height of the intermediate cage 162 a radial flange 148' which extends inwards and which carried four permanent magnets whose north poles face downwards and which are located approximately axially above the first permanent magnets. The permanent magnets 152, 154 hold that part of the arrangement mounted in gimbals in its position. In this process, the four magnets are arranged staggered at 90° and opposite to each other and with opposing poles facing.

Axially at a distance to the flange 150 the housing 148 has on the lower end coil holders 114' in, for example, soft iron. Four magnet coils 158 are positioned staggered at 90° on these coil holders 114'. In this process, each two opposite coils are switched in series so that when the current flows, one coil at a time exerts an attracting moment on the tumbling body and a neighbouring coil exerts a repelling moment. As a result of the series switching of two coils each two phases are thus produced and each phase is impressed with a sinusoidal-formed current with phase quadrature being provided. In this way an exactly circular tumbling movement of the tumbling body can be obtained when the mechanical-magnetic conditions are ideal.

FIGS. 6b and 6c represent a top view of the tumbling body with balance weight 160 and magnets and glass plate 100, while FIG. 6c shows a view of the arrangement from below.

In a circuit for the performance of this electromagnetically produced tumbling movement, e.g. for the version example in FIG. 6, an impressed sinusoidal-shaped current must be supplied on two separate channels with the signals being in phase quadrature with each other. This phase displacement may, of course, not vary with varying frequencies corresponding to a varying speed of rotation. The current amplitude in this process must be adjustable so that any desired tilt angle can be set.

Figure 7:
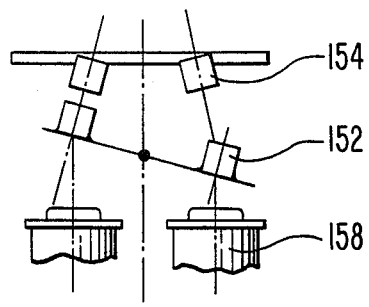
FIG. 7 shows a variation of the magnet arrangement.

FIG. 7 illustrates in schematic form another possibility for the arrangement of the fixed-position magnets. To prevent the magnets from sticking fast, the magnets 154 fixed in position on the housing in this version example are positioned so that they face diagonally outwards and downwards. When the tumbling body swings out widely and so the magnets 152 which are connected fast to the tumbling body come into a highly sloping position, then in the arrangement shown in FIG. 7 they are in such an extreme position at the most approximately axial to these. In this process, the front surfaces of magnets are positioned plano to each other and it is not possible for the magnets to stick together, but rather the magnets will repel each other due to their opposing poles. In addition, the magnets can also be positioned diagonally for a better distribution of the field lines.

Figure 8:
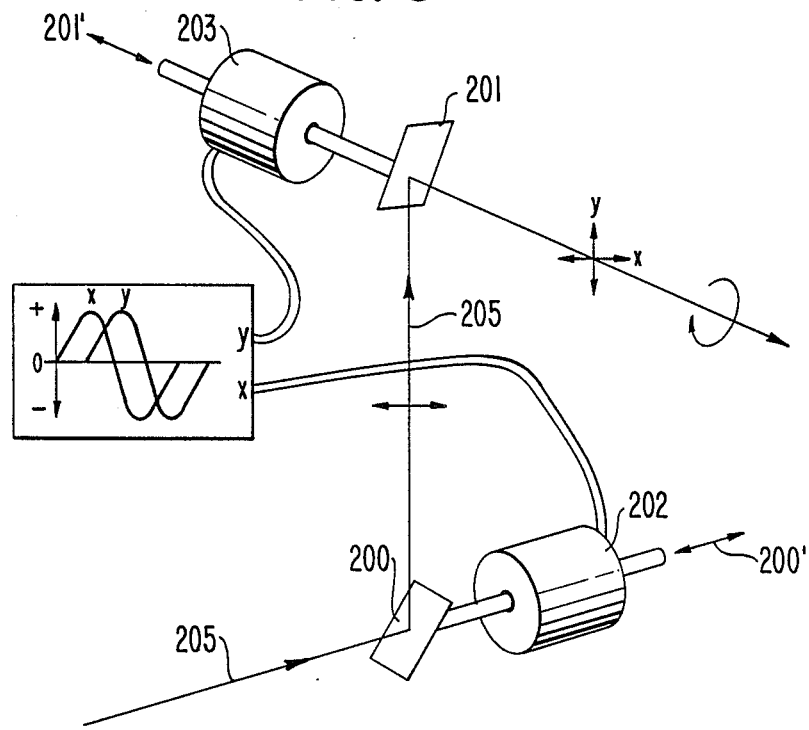
FIG. 8 shows a version example with x/y scanning.

FIG. 8 shows a further device in accordance with the invention which has as its optical part two mirrors 200 and 201, which are set to oscillate in the direction of the arrows 200', 201' by axially oscillating elements 202 and 203. If the axially oscillating elements 202 and 203 are controlled with sinusoidal signals in phase quadrature, then the laser beam 205 also scans the desired beam spot in ring form.

We claim:

1. A device for generating a circular laser beam spot of adjustable size in the human eye for laser treatment of the eye, comprising:
   focusing means for imaging a laser beam to provide a small focusing spot with a large aperture angle on a portion of the eye;
   deflector means for moving the focusing spot over a desired beam spot area of the eye in accordance with a predetermined scanning pattern so as to enable laser surgery of the eye with the circular laser beam spot of adjustable size and large aperture angle; and
   control means for controlling the deposited energy of the laser beam over the scanned area of the laser beam spot to be substantially constant.

2. A device according to claim 1, wherein the deflector means moves the focusing spot of the laser beam linearly over the desired beam spot area.

3. A device according to claim 1, wherein the deflector means moves the focusing spot of the laser beam over the desired beam spot area in a circular ring path.

4. A device according to claim 2 or 3, wherein the control means includes means for varying the power of the laser beam in dependence on local variations so as to enable generation of a predetermined power density profile over the scanned beam spot area.

5. A device according to claim 4, wherein the means for varying the power of the laser beam increases the power of the laser beam with an increasing circular ring diameter.

6. A device according to claim 4, wherein the control means further controls the deflector means to decrease revolutions of the circular movement of the focusing spot of the laser beam with an increasing circular ring diameter.

7. A device according to claim 1, wherein the deflector means includes a least one movable optical part in a beam path of the laser beam for enabling movement of the focusing spot of the laser beam over the beam spot area in the predetermined scanning pattern.

8. A device according to claim 7, wherein the deflector means includes a tumbling unit means.

9. A device according to claim 8, wherein the tumbling unit means enables rotational movement about a first axis and a tilting movement about a second axis.

10. A device according to claim 7, wherein the optical part includes two swivel plano plates positioned one above the other and having swivel axes thereof forming a predetermined angle, the plano plates being swivelled out-of-phase about the swivel axes by a drive means.

11. A device according to claim 10, wherein the swivel axes of the two plano plates form an angle of 90°, and the drive means include two angle engines controlled with sinusoidal signals in phase quadrature to each other.

12. A device according to claim 7, wherein the optical part includes a mirror.

13. A device according to claim 7, wherein the optical part includes a plano plate.

14. A device according to claim 7, wherein the optical part is mounted for swiveling movement about two swivel axes.

15. A device according to claim 7, further comprising drive engine means with revolution control for rotating the optical part about one swivel axis.

16. A device according to claim 15, further comprising another drive engine means for enabling tilting movement of the optical part about another swivel axis.

17. A device according to claim 15, further comprising means for manually tilting the optical part about another swivel axis.

18. A device according to claim 7, wherein the optical part includes two mirrors having swivel axes thereof forming an angle of 90° for enabling one of linear scanning of the beam spot area and oscillation in the direction of the laser beam for enabling a circular, ring-shaped scanning.

19. A device according to claim 7, further comprising magnetic means for enabling movement of the optical path.

20. A device according to claim 19, wherein the magnetic means includes means for holding the optical part and including a first magnet arrangement, a second magnet arrangement having stationary single magnetic element means for cooperating with the first magnet arrangement, the single magnetic element means cyclically attracting and repulsing for generating a tumbling motion of the optical part.

21. A device according to claim 20, further comprising a third stationary magnet arrangement disposed in opposition to the second magnet arrangement for repelling the first magnet arrangement.

22. A device according to claim 21, wherein the first and third magnet arrangements comprise permanent magnets and the single magnetic element means of the second magnet arrangement comprise coils.

23. A device according to claim 22, wherein the number of coils is at least three and the coils are impressed with a current out-of-phase to one another.

24. A device according to claim 1, further comprising means for providing a target light beam for movement on a path surrounding the spot to be processed.

25. A device according to claim 24, wherein when the laser beam spot is provided by a laser emitting light in the non-visible part of the spectrum, the means for providing the target light beam is an additional target laser utilized as the light source for the target light beam.

26. A device according to claim 25, wherein the laser is a helium-neon laser.

27. A device according to claim 24, wherein the target light beam means guides the beam of the target light on a circular ring path which surrounds the circular spot to be processed concentrically.

28. A device according to claim 25, wherein the focusing means focuses a laser beam of one of an EXIMER laser, a Neodym-YAG laser and a laser with a radiation wavelength of approximately 3 $\mu$m.

29. A device according to claim 24, further comprising high speed optical means in the optical beam path of the laser beam.

30. A device according to claim 1, wherein the large aperture angle is a predetermined angle which is constant independent of the size of the circular laser beam spot.

31. A device according to claim 1, wherein the control means includes at least one of means for varying the energy of the laser beam in accordance with the location of the laser beam spot on the eye and means for varying the speed at which the laser beam spot moves over the scanned area of the eye so as to control the deposited energy of the laser beam over the scanned area to be substantially constant.

32. A device according to claim 31, wherein the control means includes both the energy varying means and the speed varying means.

* * * * *